(12) United States Patent
Choi et al.

(10) Patent No.: US 8,788,227 B2
(45) Date of Patent: Jul. 22, 2014

(54) MEASURING METHOD OF CRITICAL CURRENT DENSITY OF SUPERCONDUCTOR WIRES USING MEASUREMENT OF MAGNETIZATION LOSS

(75) Inventors: Kyeong Dal Choi, Seoul (KR); Ji Kwang Lee, Wanju-gun (KR); Woo Seok Kim, Seoul (KR); Chan Park, Seoul (KR); Byung Wook Han, Anyang-si (KR); Se Yeon Lee, Suwon-si (KR)

(73) Assignees: Korea Polytechnic University Industry Academic Cooperation Foundation, Siheung-si (KR); Woosuk University Industry Academic Cooperation Foundation, Wanju-gun (KR)

( * ) Notice: Subject to any disclaimer, the term of this patent is extended or adjusted under 35 U.S.C. 154(b) by 569 days.

(21) Appl. No.: 12/997,055

(22) PCT Filed: Jul. 28, 2010

(86) PCT No.: PCT/KR2010/004957
§ 371 (c)(1),
(2), (4) Date: Dec. 9, 2010

(87) PCT Pub. No.: WO2011/062350
PCT Pub. Date: May 26, 2011

(65) Prior Publication Data
US 2011/0270557 A1   Nov. 3, 2011

(30) Foreign Application Priority Data

Nov. 20, 2009 (KR) .................. 10-2009-0112316

(51) Int. Cl.
*G01R 27/00* (2006.01)
*G01R 33/12* (2006.01)

(52) U.S. Cl.
CPC .................. *G01R 33/1246* (2013.01)
USPC .......................................... 702/65

(58) Field of Classification Search
CPC ................... G01R 33/1246; G01R 33/1238
USPC ........................................... 702/65
See application file for complete search history.

(56) References Cited

U.S. PATENT DOCUMENTS 5,132,279 A * 7/1992 Israelsson et al. ............ 505/310

OTHER PUBLICATIONS

Mikitik et al., "Asymmetry of magnetic-field profiles in superconducting strips" Phys. Rev B, 72, (2005) pp. 064506-1-064506-9.*

(Continued)

*Primary Examiner* — Jonathan C Teixeira Moffat
*Assistant Examiner* — Regis Betsch
(74) *Attorney, Agent, or Firm* — NSIP Law

(57) ABSTRACT

A method for measuring critical current density of superconductor wires according to the present invention is characterized in that it includes: (a) applying an external magnetic field to the superconductor wires, (b) measuring a magnetization loss of the superconductor wires according to the application of the external magnetic field, (c) normalizing the measured magnetization loss, and then calculating a fully-penetration magnetic field of the superconductor wires according to the normalized magnetization loss, (d) calculating a critical current density of the superconductor wires according to the calculated fully-penetration magnetic field. Therefore, the critical current density of parallel superconductor wires such as stacked superconductor wires may be measured without applying current to the superconductor wires directly.

2 Claims, 7 Drawing Sheets

(56) References Cited

OTHER PUBLICATIONS

Tsukamoto, "AC losses in a type II superconductor strip with inhomogeneous critical current distribution", Supercond. Sci. Technol., 18 (2005) pp. 596-605.*

Lee et al., "Estimtion of the Critical Current Density From the Measured Values of Perpendicular Magnetization Losses in HTS Coated Conductors", IEEE Trans. On Appl. Supercond. vol. 21. No. 3 Jun. 2011 pp. 2345-2348.*

Brandt et al., "Type II Superconducting Strip in Perpendicular Magnetic Field", Europhys. Lett. 22 (1993) pp. 735-740.*

Banno et al, "Penetration Loss in BSCCO Tape without Transport Current", IEEE Trans. on Appl. Supercond. vol. 9 (1999) pp. 2565-2568.*

Brandt et al., "Type-II-superconductor strip with current in a perpendicular magnetic field", 1993, Phys. Rev. B vol. 48, No. 17, pp. 12893-12906.*

Brandt et al. "Type-II-superconductor strip with a perpendicular magnetic field" Physical review B, vol. 48, issue 17, 1993 (5 pages, in English).

* cited by examiner

MEASURING METHOD OF CRITICAL CURRENT DENSITY OF SUPERCONDUCTOR WIRES USING MEASUREMENT OF MAGNETIZATION LOSS

CROSS-REFERENCE TO RELATED APPLICATION(S)

This application is a National Stage entry into the United States of International Application No. PCT/KR2010/004957, filed on Jul. 28, 2010, which claims the benefit of Korean Patent Application No. 10-2009-0112316, filed on Nov. 20, 2009, in the Korean Intellectual Property Office, the entire disclosure of which is incorporated herein by reference for all purposes.

BACKGROUND

1. Field

The following description relates to a method for measuring critical current density of superconductor wires using measurement of magnetization loss, in particular to a method for measuring critical current density of superconductor wires by the measurement of the magnetization loss, which is capable of estimating critical current of the superconductor wires using the measured value of the magnetization loss of the superconductor wires.

2. Description of Related Art

The advent of superconductor wires or high temperature superconductor (HTS) wires triggers the research and development of power appliance using the superconductor wires.

Unlike general power appliances using a copper, the power appliance using the superconductors requires a cooling system to maintain the characteristics of the superconductor wires. Therefore, the superconductor wires must be developed that can be used for the power appliance having high capacity and efficiency so as to secure economical efficiency of the superconductor appliance as compared to general power appliances.

Meanwhile, during the research and development of the power appliance using superconductor wires, the development of laminated wires for the large current application and of split-type wires which are formed by separating superconductor layers electrically for the reduction of AC loss is one of the main techniques that must precede other techniques for the development of power appliances requiring low-loss large current density such as superconductor transformer.

In case of the laminated superconductor wires for large current application and for low loss, however, it is difficult to measure critical current, which is necessary for the evaluation of the characteristics of superconductor wires, since the disproportion of current occurs as to the current distribution into each wire during the measurement through the application of electrical current and thus samples can be damaged.

If it is possible to estimate the density of critical current of superconductor wires without applying current physically, the above problems preferably would be prevented.

SUMMARY

In one general aspect, there is provided a method for measuring critical current density of superconductor wires, the method including: (a) applying an external magnetic field to the superconductor wires, (b) measuring a magnetization loss of the superconductor wires, according to the application of the external magnetic field, (c) normalizing the measured magnetization loss, and then calculating a fully-penetration magnetic field of the superconductor wires according to the normalized magnetization loss, and (d) calculating a critical current density of the superconductor wires according to the calculated full-penetration magnetic field.

In the method for measuring critical current density of superconductor wires, at (b), a Brandt's strip model equation may be applied to the calculation for measuring the magnetization loss of the superconductor wires.

In the method for measuring critical current density of superconductor wires, (c) may include: (c1) normalizing the measured magnetization loss, (c2) differentiating the normalized magnetization loss, and (c3) calculating a full-penetration magnetic field by determining a relation of the characteristic magnetic field applied to the Brandt's strip model equation and the full-penetration magnetic field, according to a differentiated value of the normalized magnetization loss.

In the method for measuring critical current density of superconductor wires: at (c3), the relation of the characteristic magnetic field and the full-penetration magnetic field may be expressed as an equation $B_d = \beta \times B_p$, where $B_d$ is a characteristic magnetic field, $B_p$ is a full-penetration magnetic field, and $\beta$ is a ratio of the external magnetic field to the characteristic magnetic field, and the $\beta$ may be determined to be the value when the differentiated value of the magnetization loss becomes zero at (c2).

In the method for measuring critical current density of superconductor wires, at (d), the critical current density may be expressed by an equation $$J_c = \frac{\beta B_p \pi}{\mu_0 d},$$

where $J_c$ is a critical current density, and d is a width of the superconductor wires.

Other features and aspects may be apparent from the following detailed description, the drawings, and the claims.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. The progression of processing steps and/or operations described is an example; however, the sequence of steps and/or operations is not limited to that set forth herein and may be changed as is known in the art, with the exception of steps and/or operations necessarily occurring in a certain order. Also, descriptions of well-known functions and constructions may be omitted for increased clarity and conciseness.

The method for measuring critical current density of superconductor wires according to embodiments is characterized in that it may include: (a) applying an external magnetic field to the superconductor wires, (b) measuring a magnetization loss of the superconductor wires according to the application of the external magnetic field, (c) normalizing the measured magnetization loss, and then calculating a fully-penetration magnetic field of the superconductor wires according to the normalized magnetization loss, (d) calculating a critical current density of the superconductor wires according to the calculated fully-penetration magnetic field.

According to embodiments, a measuring method of critical current density of superconductor wires using measurement of magnetization loss, capable of measuring critical current density of parallel superconductor wires such as stacked superconductor wires, without applying current to the superconductor wires physically may be provided.

The method for measuring critical current density of superconductor wires 100 may include the application of the external magnetic field to the superconductor wires, the measurement of the magnetization loss of the superconductor wires according to the application of the external magnetic field, and the calculation of the critical current density of the superconductor wires 100 by the measured magnetization loss.

Figure 1:
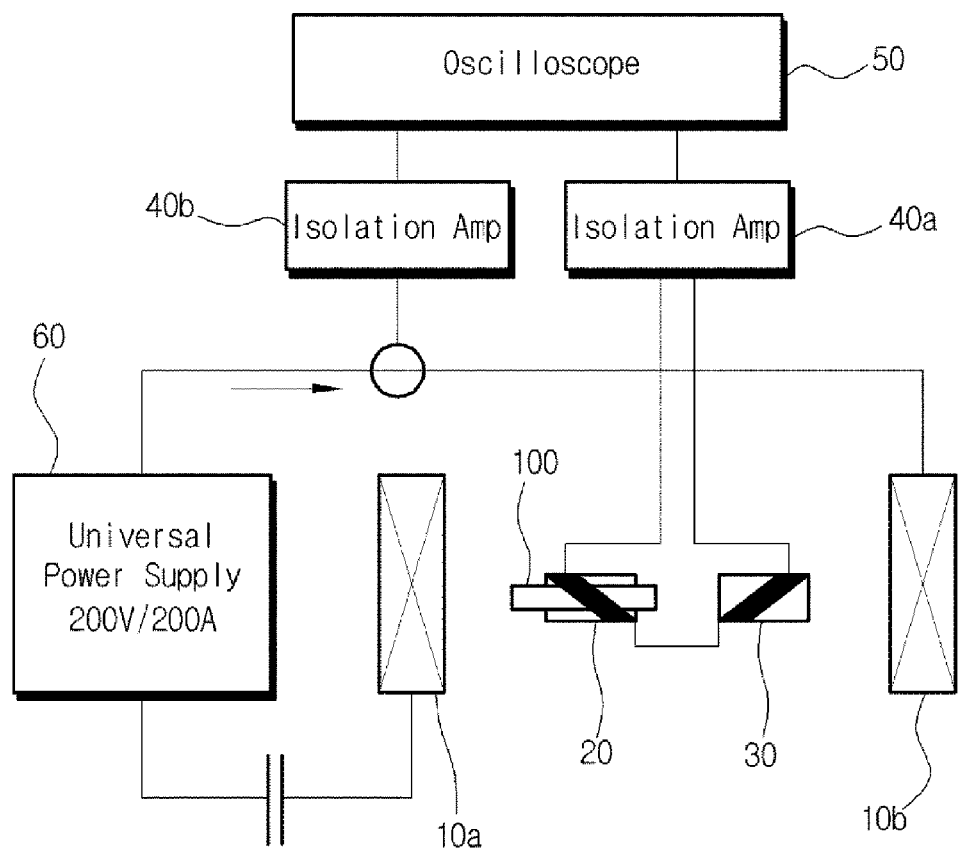
FIG. 1 represents an example of a magnetization loss measurement system for measuring magnetization loss of superconductor wires in a method for measuring critical current density of superconductor wires using the magnetization loss measurement in accordance with the present invention.

For example, an external magnetic field may be applied to the superconductor wires 100 to be measured, and the magnetization loss of the superconductor wires 100 by the application of the external magnetic field may be measured. FIG. 1 shows an example magnetization loss measurement system for measuring magnetization loss of superconductor wires 100 in a method for measuring critical current density of superconductor wires 100 in accordance with an embodiment.

As shown in FIG. 1, the magnetization loss measurement system may include a pair of magnets 10a, 10b for the application of external magnetic field, and a power supply 60 for providing the pair of magnets 10a, 10b with power such that magnetic field may be generated between a pair of magnets 10a, 10b and then the external magnetic field may be applied to the superconductor wires 100.

For example, the superconductor wires 100 may be located in a pick-up coil 20, and in response to the external magnetic field being applied, the voltage induced to the pick-up coil 20 may be generated by the sum of the magnetic field from the superconductor wires 100 and the external magnetic field. Therefore, to obtain only the magnetic field from the superconductor wires 100, the induced electromotive force by the external magnetic field may be compensated by the connection of the compensation coils 30 having the same turns as the pick-up coils 20 to the pick-up coils 20.

The system for measuring the magnetization loss may comprise a pair of isolation amplifier 40a, 40b and a digital measuring device such as an oscilloscope 50, as shown in FIG. 1. In accordance with an embodiment, by the application of the external magnetic field to the superconductor wires 100, the magnetization loss of the superconductor wires 100 may be determined by the inflow and outflow of generated energy. For example, the magnetization loss per a unit length, per a cycle, $Q_m$ may be expressed as the following Equation 1.

$$Q_m = \oint_s \vec{E} \times \vec{H} \cdot \vec{ds} \qquad \text{[Equation 1]}$$

For example, $\vec{E}$ is an electric field generated along the superconductor wires 100, and $\vec{H}$ is an intensity of the magnetic field according to the external magnetic field.

Also, the following Equation 2 may be derived by expressing Equation 1 in the form of the magnetization loss of the superconductor wires 100 per a unit volume, per a cycle, $Q_m$ using the measured voltage and current.

$$Q_m = \frac{C_{pu}k}{V_s} \int_0^T v(t)i(t)dt \qquad \text{[Equation 2]}$$

For example, k is a magnetic constant representing magnetic flux density per unit current of the magnet 10a, 10b used to generate the external magnetic field, and $C_{pu}$ is a correction constant of the pick-up coils 20, and $V_s$ is a volume of the superconductor wires 100, t is a time, and T is a period.

Figure 2:
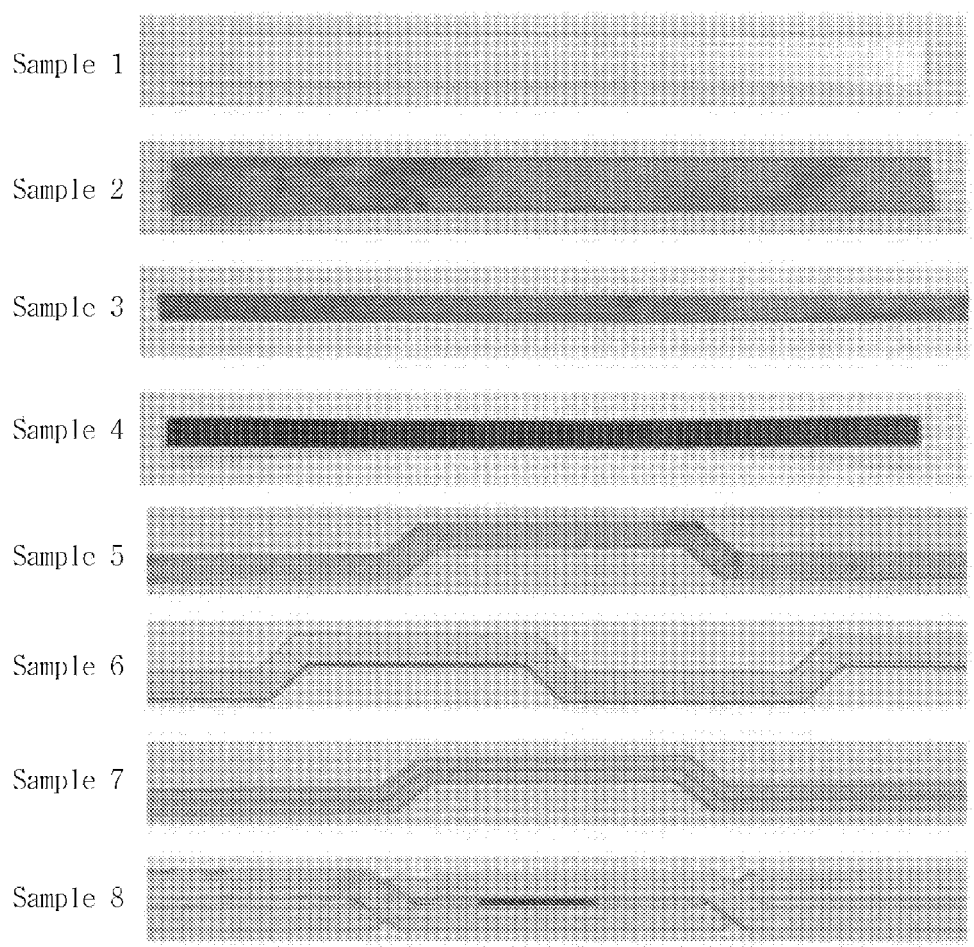
FIG. 2 represents an example of a superconductor wire sample for applying the method of measuring critical current density of superconductor wires using the measurement of magnetization loss in accordance with the present invention.

Using the above constitution, an experiment to measure the magnetization loss of the superconductor wires 100 was performed. The detailed specifications of the superconductor wires 100 used for the experiment to measure the magnetization loss is shown in the following Table 1, and the shape of the superconductor wires 100 is shown in FIG. 2.

TABLE 1

| | Sample1 | Sample2 | Sample3 | Sample4 |
|---|---|---|---|---|
| Type | SF12050 | SCS12050 | SCS4050 | 344C |
| Width [mm] | 12 | 12 | 4 | 4.3 |
| Thickness [mm] | 0.05 | 0.095 | 0.095 | 0.2 |
| Stabilizer | — | Cu, 40 μm | Cu, 40 μm | Cu, 100 μm |
| Substrate | Hastelloy | Hastelloy | Hastelloy | Ni5% W |

| | Sample5 | Sample6 | Sample7 | Sample8 |
|---|---|---|---|---|
| Type | F1_N1_4.5 | F1_N1_5.3 | F2_N1_5.3 | F1_N2_5.3 |
| Width [mm] | 4.5 | 5.3 | 5.3 | 10.6 |
| Thickness [mm] | 0.05 | 0.05 | 0.05 | 0.05 |
| Stabilizer | — | — | — | — |
| Substrate | Hastelloy | Hastelloy | Hastelloy | Hastelloy |

For example, samples may be provided such as superconductor wires 100 comprising a copper stabilizing layer and being 12 mm and 4 mm in width, superconductor wires 100 having no copper stabilizing layer and being 12 mm in width, superconductor wires 100 having a copper stabilizing layer and being 4.3 mm in width, three types of wires for transposition stacked wires and one type of stacked wire that are prepared for low-loss stacked wires for large current. The wires for transposition stacked wires may be prepared in such a manner that wires having a copper stabilizing layer and being 12 mm in width are cut into wires having width of 4.5 mm and 5.3 mm.

Figure 3:
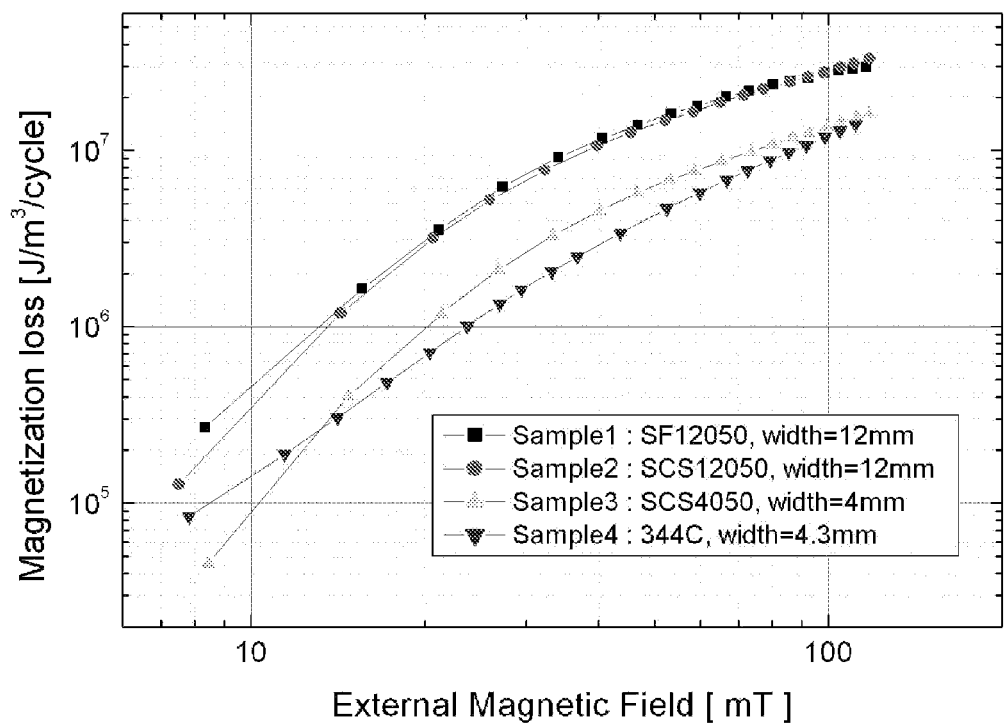
FIGS. 3 and 4 are graphs showing the measurement of the magnetization loss for the samples of FIG. 2 measured by the system for measuring magnetization loss of FIG. 1.
Figure 4:
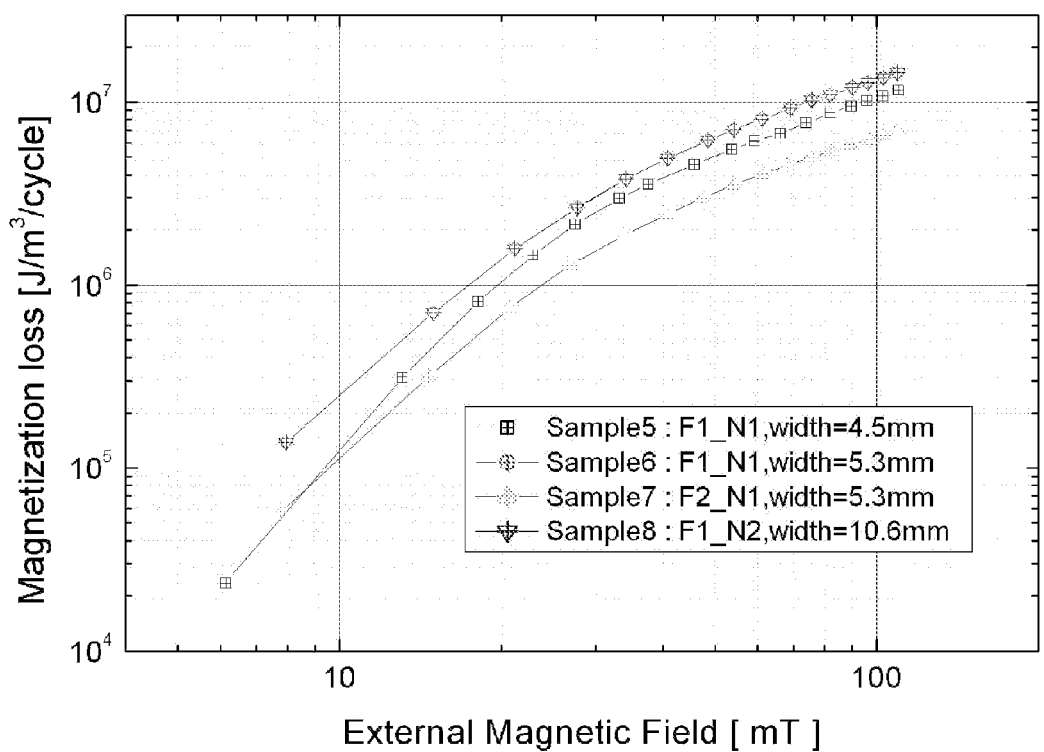

FIG. 3 is a graph showing measured value of the magnetization loss for the samples 1 to 4 according to the measuring method as explained above, and FIG. 4 is a graph showing the measured value of the magnetization loss for the samples 5 to 8 according to the measuring method as explained above.

A method for measuring the critical current density of the superconductor wires 100 using, magnetization loss of the superconductor wires 100 measured by the above process will be described.

An embodiment may use Brandt's strip modeling equation shown in the following Equation 3, for the calculation of magnetization loss by external magnetic field applied in the vertical direction of the superconductor wires 100. Brandt's strip model equation is disclosed in 'Type-II—superconductor strip with a perpendicular magnetic field' published in 'Physical review B (vol. 48, issue 17, 1993)'.

$$Q_m = \frac{2B_m^2}{\mu_0} \frac{\pi\omega}{2\beta d} \left[ \frac{2}{\beta} \ln(\cosh\beta) - \tanh\beta \right]$$ [Equation 3]

For example, $B_m$ is a dimension for the external magnetic field, $\omega$ is a frequency, and d is a width of the superconductor wires 100. $\mu_0$ is a vacuum permeability which is a constant value, e.g., $4\pi \times 10^{-7}$. $\beta$ is a ratio of the external field to the characteristic magnetic field, which can be defined in the following Equation 4.

$$\beta = \frac{B_m}{B_d}$$ [Equation 4]

For example, $B_d$ represents a dimension of the characteristic magnetic field, which may to be defined as the following Equation 5.

$$B_d = \frac{\mu_0 J_c d}{\pi}$$ [Equation 5]

For example, $J_c$ is a critical current density of the superconductor wires 100.

If the Brandt's strip model equation in Equation 3 is normalized to confirm a fully-penetration magnetic field, it can be expressed as the following Equation 6.

$$\text{Normalized loss} = \frac{2\pi\omega}{d\beta} \left[ \frac{2}{\beta} \ln(\cosh\beta) - \tanh\beta \right]$$ [Equation 6]

$$= K \frac{1}{\beta} \left[ \frac{2}{\beta} \ln(\cosh\beta) - \tanh\beta \right]$$

Figure 5:
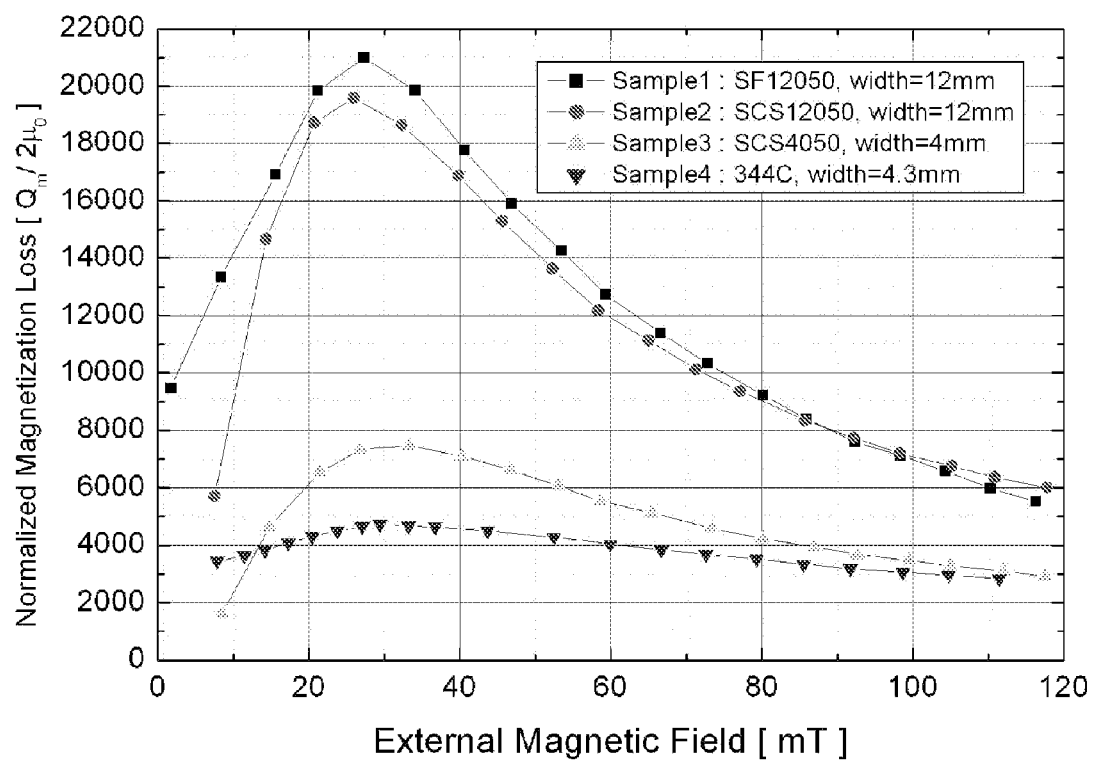
FIGS. 5 and 6 are graphs showing the measurement of normalized magnetization loss for the magnetization loss of FIGS. 3 and 4, respectively.
Figure 6:
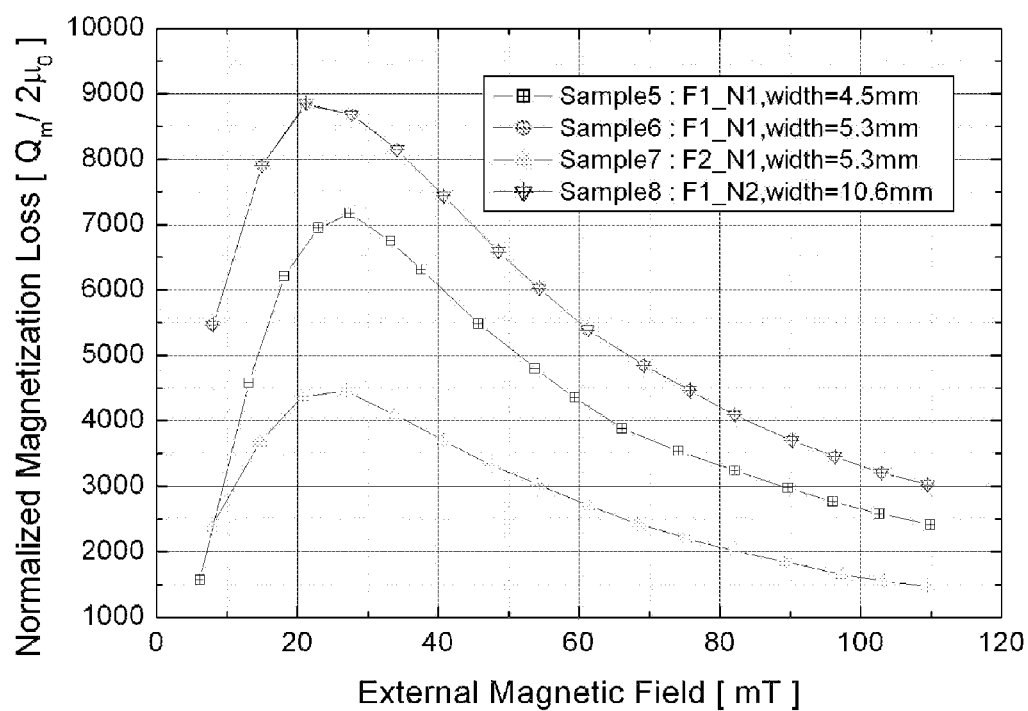

In Equation 6, $$\frac{2\pi\omega}{d}$$

may be defined as a constant K. If the normalized Equation 6 is differentiated with regard to $\beta$, it may be expressed as the following Equation 7. For example, FIGS. 5 and 6 are graphs showing the measured value of normalized magnetization loss for the magnetization loss of FIGS. 3 and 4, respectively; and FIG. 7 shows an example for the differentiated value of the normalized magnetization loss.

Differentiated value = [Equation 7]

$$-\frac{4}{\beta^3} \ln(\cosh(\beta)) + \frac{3}{\beta^2} \tanh(\beta) - \frac{1}{\beta \cosh^2(\beta)}$$

Figure 7:
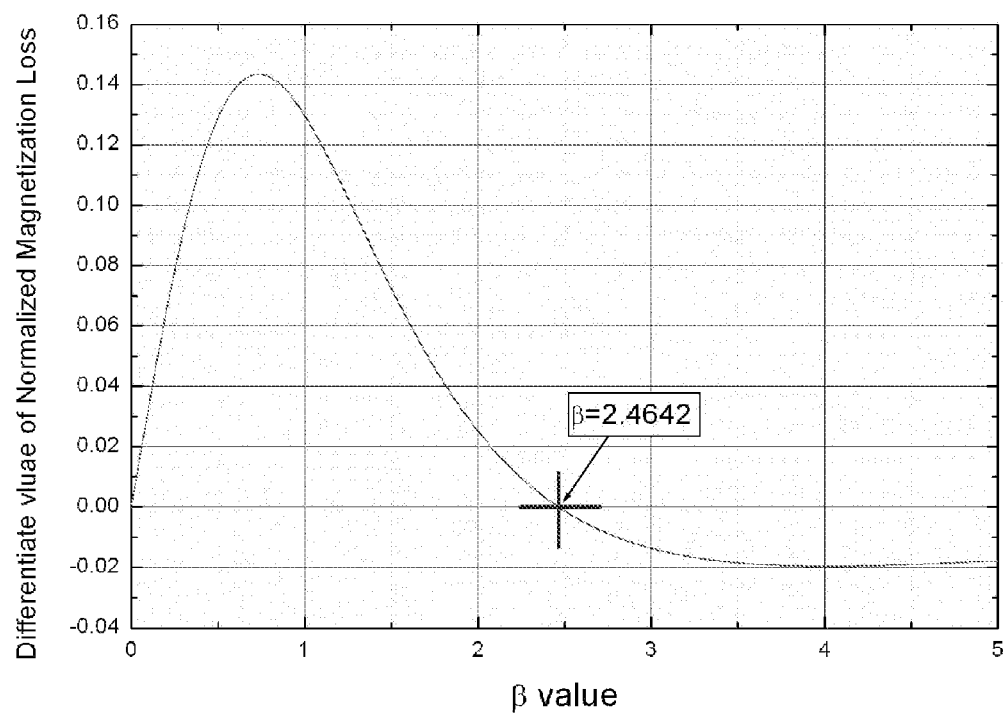
FIG. 7 represents an example for the differentiated value of the normalized magnetization loss.

As illustrated in the example of FIG. 7, it may be seen that $\beta$ is 2.4642 when a differentiated value of the normalized magnetization loss becomes zero. Therefore, in an example in which critical current density is calculated using the fully-penetration magnetic field from the normalized magnetization loss, if the critical current density is calculated with the value of $\beta$ being 2.4642, the following Equation 8 may be obtained.

$$B_d = 2.4642 \times B_p$$ [Equation 8]

As above, if the fully-penetration magnetic field is determined, it may be possible to predict the critical current density of the superconductor wires 100 as in the following Equation 9.

$$J_c = \frac{2.4642 B_p \pi}{\mu_0 d}$$ [Equation 9]

By normalizing and differentiating the Brandt's strip model equation that expresses the magnetization loss to obtain a fully-penetration magnetic field required to calculate the critical current density, it may be possible to define the relation of the fully-penetration magnetic field and the characteristic magnetic field used for the Brandt's strip model equation, and thus to to measure the critical current density.

Table 2 shows the difference of the critical current density for each sample of Table 1 calculated by the method for measuring critical current density of superconductor wires 100 according to an embodiment, and the critical current density measured physically.

As shown in Table 2, the critical current density for the samples from the method for measuring the critical current density of the superconductor wires 100 is identical to the physically measured critical current density within the error range approximately less than 5%. Meanwhile, it can be seen that the sample 4 causes 45% error, and this is because wires of the sample 4 use Ni5% W substrate, as shown in Table 1; therefore, the magnetic body influences the measurement of the magnetization loss.

TABLE 2

| | Estimated value of critical current | Measured value of critical current | Error |
|---|---|---|---|
| Sample 1 | 27.7 A/m$^2$ | 28.6 A/m$^2$ | 3.2% |
| Sample 2 | 26.3 A/m$^2$ | 24.8 A/m$^2$ | 6% |

TABLE 2-continued

|  | Estimated value of critical current | Measured value of critical current | Error |
|---|---|---|---|
| Sample 3 | 33.8 A/m² | 34.0 A/m² | 0.6% |
| Sample 4 | 29.8 A/m² | 20.5 A/m² | 45% |
| Sample 5 | 27.3 A/m² | 26.8 A/m² | 1.9% |
| Sample 6 | 27.7 A/m² | 27.9 A/m² | 0.7% |
| Sample 7 | 27.3 A/m² | 25.7 A/m² | 5.8% |
| Sample 8 | 21.5 A/m² | 22.0 A/m² | 2.3% |

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for measuring critical current density of superconductor wires, the method comprising:

(a) applying an external magnetic field to the superconductor wires;

(b) measuring a magnetization loss of the superconductor wires, according to the application of the external magnetic field;

(c) normalizing the measured magnetization loss, and then calculating a full-penetration magnetic field of the superconductor wires according to the normalized magnetization loss; and (d) calculating a critical current density of the superconductor wires according to the calculated full-penetration magnetic field, wherein:

at (b), a Brandt's strip model equation $$Q_m = \frac{2B_m^2}{\mu_0} \frac{\pi\omega}{2\beta d}\left[\frac{2}{\beta}\ln(\cosh\beta) - \tanh\beta\right]$$

is applied to the calculation for measuring the magnetization loss of the superconductor wires, where $Q_m$ is the magnetization loss by the external magnetic field applied in a vertical direction of the superconductor wires, $B_m$ is a dimension for the external magnetic field, $\omega$ is a frequency, $\beta$ is a ratio of the external magnetic field to a characteristic magnetic field, $\mu_0$ is a vacuum permeability which is a constant value, and d is the width of the superconductor wires;

and further wherein operation (c) comprises:

(c1) normalizing the measured magnetization loss;

(c2) differentiating the normalized magnetization loss; and (c3) calculating the full-penetration magnetic field by determining a relation of the characteristic magnetic field applied to Brandt's strip model equation and the full-penetration magnetic field, according to a differentiated value of the normalized magnetization loss, and further wherein at (c3), the relation of the characteristic magnetic field and the full-penetration magnetic field is expressed as an equation $B_d=\beta \times B_p$, where $B_d$ is the characteristic magnetic field, $B_p$ is the full-penetration magnetic field, and $\beta$ is the ratio of the external magnetic field to the characteristic magnetic field;

and further wherein $\beta$ is determined when the differentiated value of the normalized magnetization loss becomes zero at (c2).

2. The method for measuring critical current density of superconductor wires of claim 1, wherein, at (d), the critical current density is expressed by an equation $$J_c = \frac{\beta B_p \pi}{\mu_0 d},$$

where Jc is the critical current density.

* * * * *